US00PP08525P

United States Patent [19]

Trees

[11] Patent Number: Plant 8,525

[45] Date of Patent: Dec. 28, 1993

[54] GERANIUM PLANT 'DESIGNER HOT PINK'

[75] Inventor: Scott C. Trees, Nipomo, Calif.

[73] Assignee: Ball Floraplant, West Chicago, Ill.

[21] Appl. No.: 996,117

[22] Filed: Dec. 23, 1992

[51] Int. Cl.[5] ..... A01H 5/00
[52] U.S. Cl. ..... Plt./87.12
[58] Field of Search ..... Plt./87.12

[56] References Cited

U.S. PATENT DOCUMENTS

P.P. 7,599 7/1991 Trees ..... Plt. 87.12
P.P. 8,128 2/1993 Trees ..... Plt. 87.12

*Primary Examiner*—James R. Feyrer
*Attorney, Agent, or Firm*—Arnold, White & Durkee

[57] ABSTRACT

Geranium Designer Series TM Hot Pink (BFP-114) is a new and distinct cultivar of geranium, botanically known as *Pelargonium* × *hortorum* Bailey, and hereinafter referred to by the cultivar name Designer Hot Pink. Designer Hot Pink was selected from self-pollination of the tetraploid breeding line PAS-B. The new cultivar is distinguished from its parent and from other geraniums by its bright pink color with a white eve on the upper petals, high degree of weather tolerance and resistance to botrytis.

1 Drawing Sheet

BACKGROUND OF THE NEW PLANT

Designer Hot Pink is a product of a planned breeding program which had the objective of creating new geranium cultivars with large florets and umbels, bright color, good weather tolerance, fast rooting, good shipping qualities and compact basal branching character without using growth regulators.

Designer Hot Pink originated from a self-pollination made in a controlled breeding program in West Chicago, Ill. Designer Hot Pink resulted from a self pollination of the tetraploid breeding line, PAS-B.

Female PAS-B is a proprietary breeding parent used in a breeding program. It is not commercially available. PAS-B is a semi-double, pink with medium green foliage. By comparison, Designer Hot Pink is a clear pink without any blue in the color compared to PAS-B which can show pink flowers with a blue undertone.

Designer Hot Pink was discovered and selected as one flowering plant within the progeny of the stated self-pollination by the inventor in a controlled environment in Santa Maria, Calif.

The first act of asexual reproduction of Designer Hot Pink was accomplished when vegetative cuttings were taken from the initial selection in a controlled environment in Santa Maria, Calif. by a technician supervised by the inventor. Horticultural examination of selected units demonstrated that the combination of characteristics as herein disclosed for Designer Hot Pink are firmly fixed and are retained through successive generations of asexual reproduction.

Designer Hot Pink has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commercial practice.

The following traits have been repeatedly observed and are determined to be basic characteristics of Designer Hot Pink which in combination distinguish this geranium as a new and distinct cultivar. These traits include basal branching without growth regulators, a spreading-mounded habit, lack of fruits, an unusually high resistance to botrytis.

Of the many commercial cultivars known to the present inventor, the most similar in comparison to Designer Hot Pink is Hot Pink Satisfaction (U.S. Plant Pat. No. 8,128). The bright pink flower color of Hot Pink Satisfaction is similar to Designer Hot Pink, but Designer Hot Pink corolla are distinguished with a white eye on the upper petals and darker veins. In contrast to Hot Pink Satisfaction, the new cultivar Designer Hot Pink has a high degree of weather tolerance and shows excellent resistance to botrytis. Designer Hot Pink has a spreading mounded appearance unlike Hot Pink Satisfaction which has upright branching.

The florets of Designer Hot Pink are more flat (less cupped) than Hot Pink Satisfaction but the petaloids of Designer Hot Pink are smaller and less numerous (0–3) than those of Hot Pink Satisfaction (3–5). Designer Hot Pink has a more compact habit when grown under field conditions. Designer Hot Pink averages 2–3 branches in a 10 cm pot compared with Hot Pink Satisfaction which averages 1.5–2.0 branches in a 10 cm pot. No pinching is required with Designer Hot Pink.

DESCRIPTION OF THE PHOTOGRAPH

The accompanying color photographs show a top view of the typical flower and foliage characteristics of Designer Hot Pink. The view taken against a dark background illustrates flower color closest to the color values assigned from The Royal Horticultural Society Color Chart. The view taken against a light background highlights the leaf characteristics.

DESCRIPTION OF THE PLANT

In the following description, color references are made to The Royal Horticultural Society Color Chart. The color values were determined between 11:00–11:30 a.m. on Nov. 10, 1992 under 600 foot candles at Arroyo Grande, Calif. USA.

Classification:

*Botanical.*—*Pelargonium* × *hortorum* Bailey.

*Commercial.*—Designer Hot Pink, Zonal Geranium.

INFLORESCENCE

Umbel:

*Average diameter.*—8.5–9.5 cm.

*Average depth.*—6.5–7.0 cm.

*Peduncle length.*—15.0–23 cm.

*Pedicel length.*—3.0–3.3 cm.

*Number umbels/plant* (designated circumstances).—14–17 on 18 week old field grown plants.

*Number of flowers/umbel.*—17–19.

Corolla:

*Petals.*—Length: 2.7–2.9 cm; width: 2.4–2.6 cm.

*No. of petals.*—5–6.

*Average diameter.*—4.5–4.7 cm.

*Form.*—Semi-double with petaloids.

*Number of petaloids.*—0–3, small, nearly inconspicuous. Bottom ⅓–½ of two upper petals is distinctly white, giving appearance of "eye" against a general background of Bright Pink (57C).

*Color (General tonality from a distance of three meters).*—Bright Pink 57C.

*Description of petal form.*—Imbricate.

*Color (abaxial).*—57C with white eye on upper petals and darker veins.

*Color (adaxial).*—62B.

Bud:

*Shape.*—Oval, hemispherical.

*Color (abaxial).*—57C.

*Color (adaxial).*—62B.

Reproductive organs:

*Androecium.*—10, 8 mm anther/filaments, 1.0–1.5 mm anther.

*Gynoecium.*—9 mm, 5 lobed stigma, 2 mm style.

*Presence or absence of fruits.*—No fruits.

Spring flowering response period: 7–8 weeks from rooted cutting.

Outdoor flower production: Freely flowering high above foliage due to longer peduncles.

Durability: High degree of weather tolerance.

Foliage:

*Leaves.*—8.0–10.0 cm at widest point: 5.0–5.5 cm at narrowest point.

*Zonation.*—Absent.

*Form.*—Reniform, cordate.

*Margin.*—Crenate.

*Color (abaxial).*—146A.

*Color (adaxial).*—146B.

*Color (zonation).*—None.

*Tolerance of botrytis.*—Excellent Botrytis resistance.

General appearance and form:

*Internode length.*—2.0–2.5 cm.

*Branching pattern.*—Spreading mounded branching.

*Height.*—25–26 cm on 18 week old plants in field.

What is claimed is:

1. A new and distinct geranium cultivar, substantially as herein described and shown, characterized by bright pink flowers with a white eye on the upper petals, a high degree of weather tolerance and excellent resistance to botrytis.

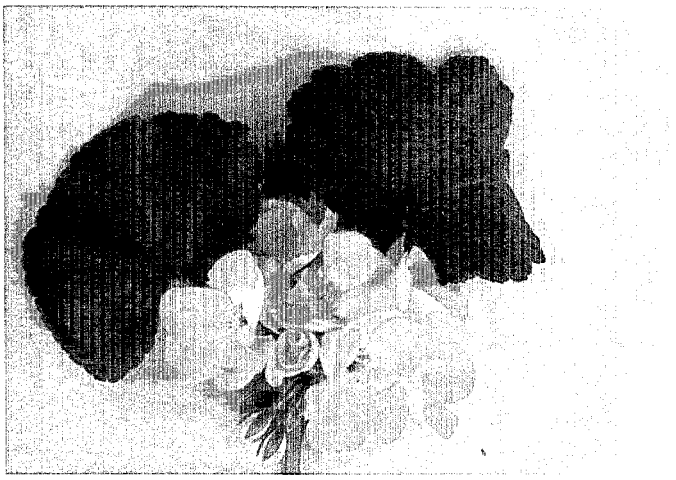
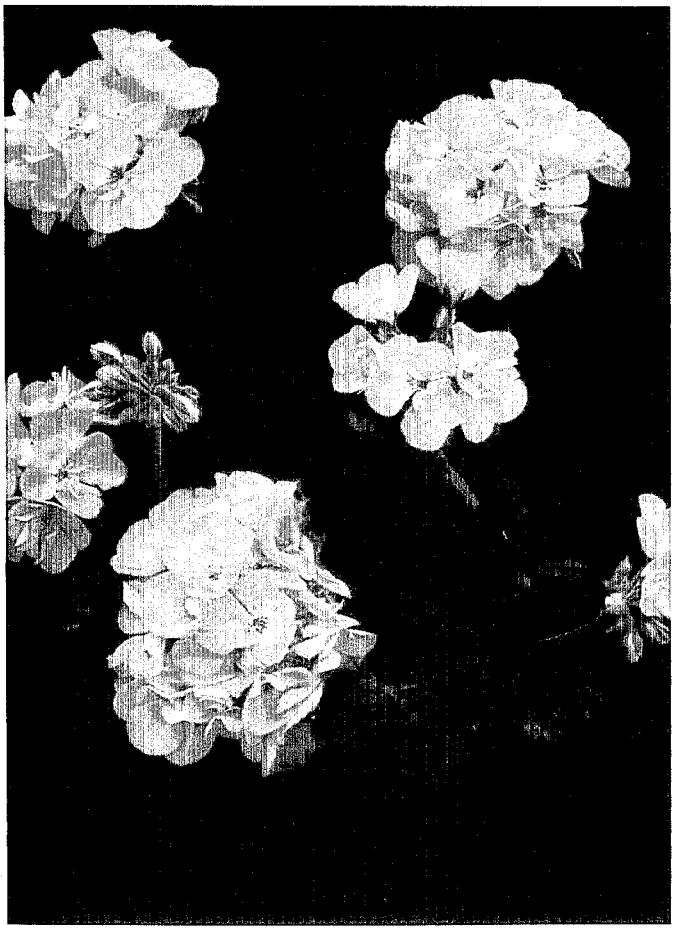

* * * * *